United States Patent [19]

Wilk et al.

[11] Patent Number: 5,522,399
[45] Date of Patent: Jun. 4, 1996

[54] CATHETERIZATION DEVICE AND ASSOCIATED ASSEMBLY

[76] Inventors: Peter J. Wilk, 185 West End Ave., New York, N.Y. 10023; Jonathan Tiefenbrun, 62 Country Rd., Mamaroneck, N.Y. 10543

[21] Appl. No.: 312,240

[22] Filed: Sep. 26, 1994

[51] Int. Cl.$^6$ .................................................... A61B 5/00
[52] U.S. Cl. ............................................................ 128/748
[58] Field of Search ................................. 128/673, 687, 128/689, 725, 727, 729, 748, 774; 604/50, 53, 100, 164

[56] References Cited

U.S. PATENT DOCUMENTS

| | | | |
|---|---|---|---|
| 2,396,351 | 3/1946 | Thompson | 128/748 |
| 3,081,770 | 3/1963 | Hunter | 128/748 |
| 4,060,074 | 11/1977 | Russo | 128/725 |
| 4,164,938 | 8/1979 | Patton | 128/748 |
| 4,299,230 | 11/1981 | Kubota | 128/748 |
| 4,314,480 | 2/1982 | Becker | 128/748 |

*Primary Examiner*—Max Hindenburg
*Attorney, Agent, or Firm*—R. Neil Sudol; Henry D. Coleman

[57] ABSTRACT

A catheterization device comprises a catheter, a hollow hypodermic needle longitudinally traversing the catheter, and a pressure detector and indicator attached to the needle at a proximal end thereof for sensing pressures inside a patient upon insertion of a distal tip of the needle into the patient and for qualitatively indicating the sensed pressure. The pressure detector and indicator includes an at least partially transparent housing, a fluid in the housing communicating with a lumen of the needle, and a movable indicator element such as a styrofoam sphere disposed in the fluid in the housing.

16 Claims, 2 Drawing Sheets

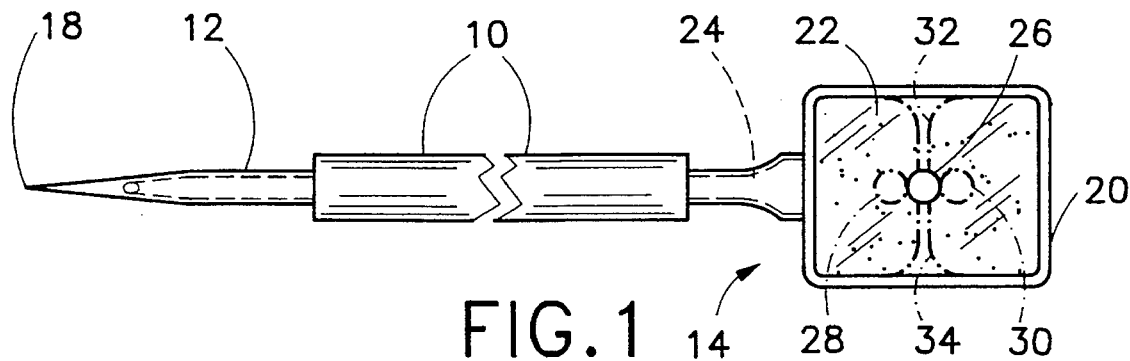
FIG. 1
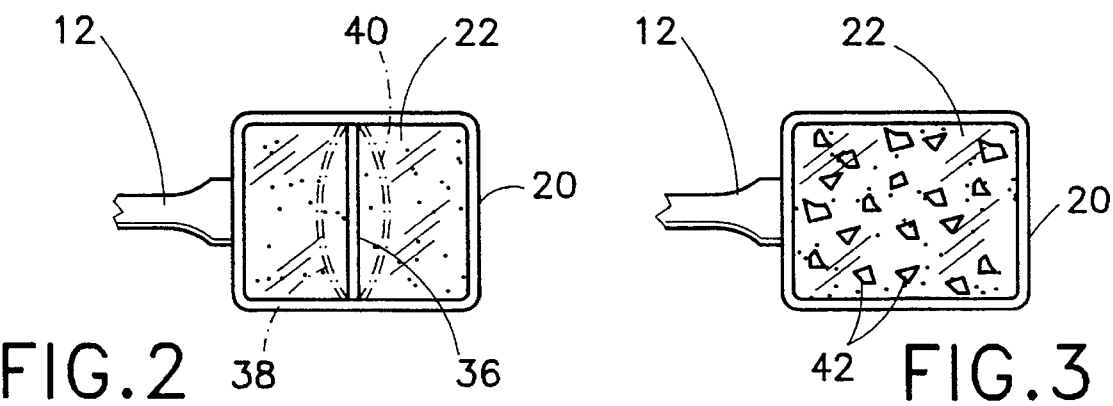
FIG. 2   FIG. 3
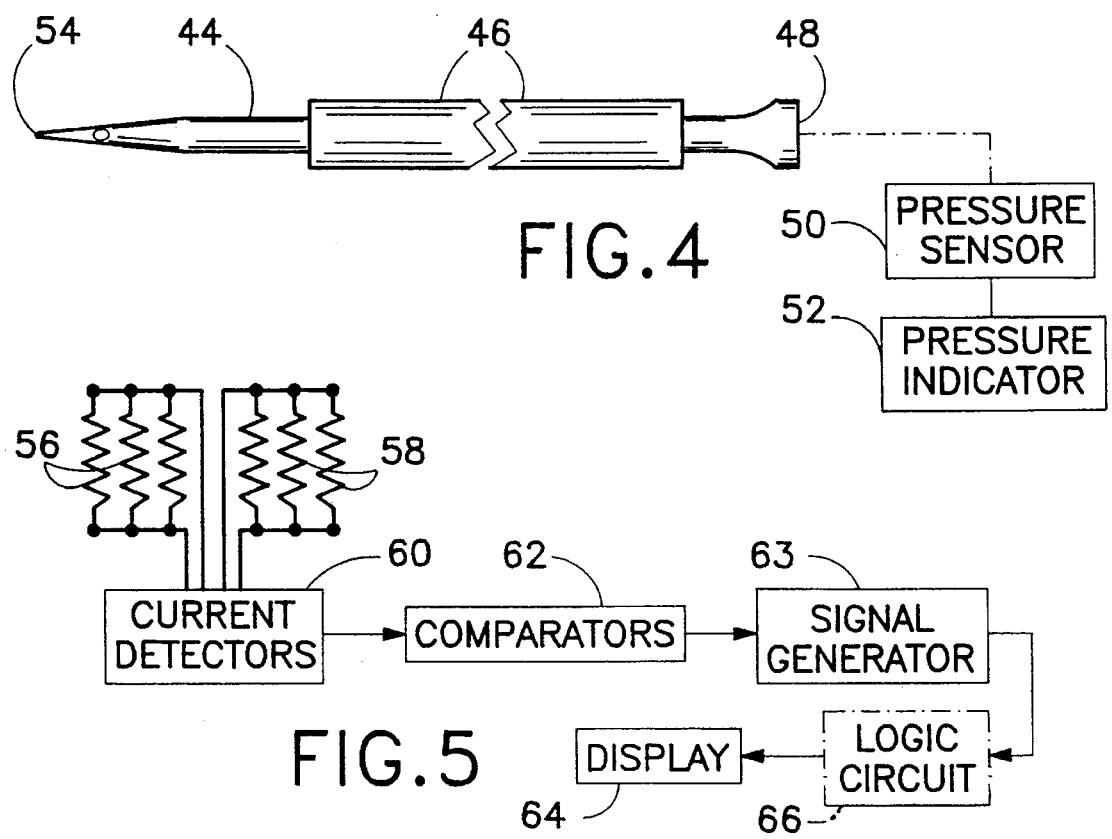
FIG. 4
FIG. 5

5,522,399

CATHETERIZATION DEVICE AND ASSOCIATED ASSEMBLY

BACKGROUND OF THE INVENTION

This invention relates to a catheterization device and an associated catheterization method.

A catheterization procedure involves inserting a catheter into a vein of a patient, for example, for purposes of feeding an intravenous fluid to the patient. The catheter is inserted over a hypodermic needle whose distal tip has been inserted into the vein. Generally, a transparent chamber is connected to the needle at the proximal end thereof. Upon insertion of the needle into a blood vessel, blood flows into the chamber, thereby providing a visual signal or indication that vascular access has been attained.

A problem with conventional catheterization procedures is that sometimes an artery is pierced, rather than a vein, particularly where the artery is located close to a targeted vein. When the needle is removed from the artery, a large hematoma may result unless proper action is taken immediately. For example, pressure applied to the patient in the area of the punctured artery can stem the flow of blood and prevent the formation of a hematoma. The problem lies in immediately recognizing that an artery has been punctured. Generally, the conventional apparatus comprising a simple transparent chamber does not enable a person of ordinary skill and experience to detect the difference between a vein and an artery.

Sometimes, where the vein sought is in the chest region, a needle is inadvertantly inserted into a lung. Because there is a negative pressure envelope which surrounds the interior lining of the lung for maintaining the lung in an expanded, functional, configuration, a substantial compromise in the integrity of that envelope causes the lung to collapse. Lung collapse can occur when the piercing of the lung is not immediately recognized.

OBJECTS OF THE INVENTION

An object of the present invention is to provide a catheterization device for facilitating the detection of needle insertion into untargeted organs.

Another object of the present invention is to provide such a device which will provide a qualitative indication of the nature of an organ pierced by a distal tip of a hypodermic needle.

Another, more particular, object of the present invention is to provide such a device which is inexpensive to manufacture and easy to use.

A further object of the present invention is to provide an associated catheterization method for facilitating the detection of needle insertion into untargeted organs and for providing a qualitative indication of the nature of an organ pierced by a distal tip of a hypodermic needle.

These and other objects of the present invention will be apparent from the drawings and detailed descriptions herein.

SUMMARY OF THE INVENTION

A catheterization device comprises, in accordance with the present invention, a catheter, a hollow hypodermic needle longitudinally traversing the catheter, and a pressure detector and indicator attached to the needle at a proximal end thereof for sensing pressures inside a patient upon insertion of a distal tip of the needle into the patient and for qualitatively indicating the sensed pressure.

According to another feature of the present invention, the pressure detector and indicator includes an at least partially transparent housing, a fluid in the housing communicating with a lumen of the needle, and a movable indicator element disposed in the fluid in the housing.

According to particular features of the present invention, the movable indicator element is a float exemplarily in the form of a styrofoam sphere disposed in the fluid.

According to a further feature of the present invention, the float is elastically connected to the housing, e.g., via a diaphragm.

In an alternative specific embodiment of the present invention, the movable indicator element is a diaphragm connected to the housing. The diaphragm exhibits a motion responsive to the internal organic pressures of the patient and accordingly indicative of those internal pressures.

According to an additional feature of the present invention, the movable indicator element is one of a plurality of movable indicator elements floating in the fluid. These indicator elements may be highly reflective particles such as tiny aluminum foil fragments.

A catheterization method in accordance with the present invention utilizes a catheter and a hollow hypodermic needle longitudinally traversing the catheter. The method comprises the steps of (a) inserting a distal end of the needle into a patient, (b) automatically sensing pressures at the distal tip of the needle upon insertion of that distal tip into the patient, and (c) automatically generating, at a proximal end of the needle, a qualitative indication of the sensed pressure.

In accordance with another feature of the present invention, the step of generating the pressure indication includes the step of moving an indicator element (eg., a spherical float) disposed in a fluid filled chamber at the proximal end of the needle.

When the sensed pressure is arterial, the indicator element is reciprocated in response to pulsating arterial pressure. Upon the reciprocation of the indicator element in the fluid medium, the needle is removed from the patient and pressure is placed on the patient at an insertion point of the needle, thereby reducing flow of blood from a punctured artery.

When the sensed pressure is negative owing to entry into a lung, the indicator element moves in a distal direction. Upon an indication of a negative pressure, particularly upon insertion of the hypodermic needle in the chest region, the needle is withdrawn and steps are taken immediately to prevent the flow of air through the hole into the patient's chest.

When the pressure indicator element moves in a proximal direction so as to signal an internal pressure in a venous range, i.e., between 10 and 20 mm Hg, the catheter is slid over the needle into the detected vein, the needle is removed and the catheter is connected to an intravenous fluid source.

The pressure indicator element also moves in a proximal direction when the distal tip of the needle is inserted into a spinal column. Upon detecting such a motion of the indicator element, a user injects an anaesthetic through the needle or through the catheter upon insertion of the catheter over the needle and subsequent removal of the needle from the spine.

A catheterization device in accordance with the present invention facilitates detection of inadvertant needle insertion into untargeted organs and thus enables medical personnel to undertake correction measures. The qualitative indication of intraorganic pressure in accordance with the present invention expedites recognition of the nature of an organ pierced by a distal tip of a hypodermic needle. For example, where the indicator element is a sphere, perception of the motion of the indicator element is easy and immediate.

A catheterization device or assembly in accordance with the present invention is inexpensive to manufacture.

BRIEF DESCRIPTION OF THE DRAWING

FIG. 1 is a schematic side elevational view, on an enlarged scale, of a hypodermic catheterization assembly in accordance with the present invention, showing a pressure sensing and indicating chamber at a proximal end of a hypodermic needle.

FIG. 2 is a schematic side elevational view of another pressure sensing and indicating chamber for use in the assembly of FIG. 1.

FIG. 3 is a schematic side elevational view of a further pressure sensing and indicating chamber for use in the assembly of FIG. 1.

FIG. 4 is partially a schematic side elevational view of a hypodermic needle and catheter and partially a block diagram of pressure sensing and indicating elements of a general embodiment of a hypodermic catheterization assembly in accordance with the present invention.

FIG. 5 is basically a block diagram showing particular functional components of electrical functional elements implementing the pressure sensing and indicating elements of the embodiment of FIG. 4.

DETAILED DESCRIPTION

Figure 6:
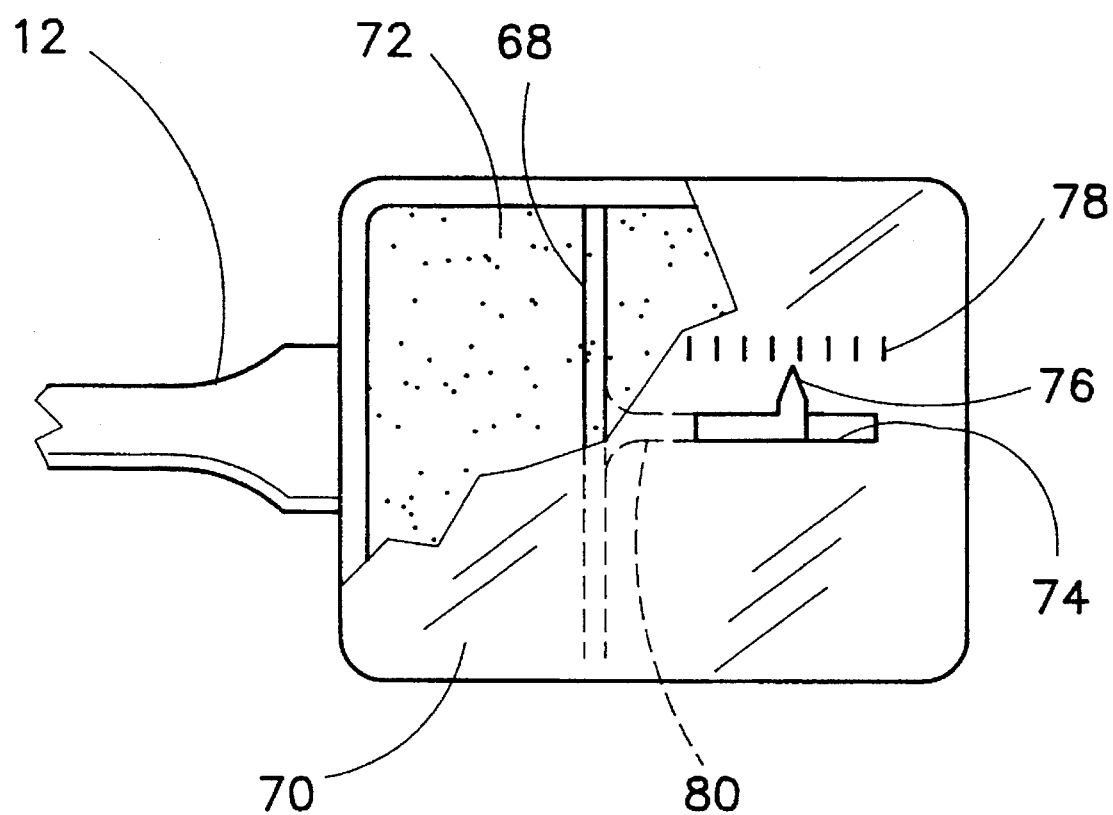
FIG. 6 is a schematic side elevational view of an additional pressure sensing and indicating chamber for use in the assembly of FIG. 1.

As illustrated in FIG. 1, a hypodermic catheterization assembly comprises a catheter 10, a hollow hypodermic needle 12 longitudinally traversing the catheter, and a pressure detector and indicator 14 attached to the needle at a proximal end thereof for sensing pressures inside a patient upon insertion of a distal tip 18 of the needle into the patient and for qualitatively indicating the sensed pressure.

Pressure detector and indicator 14 includes a transparent housing or chamber 20, a fluid 22 in the housing communicating with a lumen 24 of needle 12, and a movable indicator element 26 in the form of a styrofoam ball disposed in the fluid in the housing. Fluid 22 is a biocompatible liquid such as saline solution or a hydrogel and is disposed in needle lumen 24 as well as in housing 20. For purposes of facilitating the observation of spherical styrofoam indicator element 26 and its motion, fluid 22 may have an inherent color such as blue.

Spherical styrofoam indicator element 26 floats in fluid 22 and exhibits a motion in fluid 22 responsive to, and accordingly indicative of, intraorganic pressures existing at distal tip 18 of needle 12 particularly upon insertion of the distal tip into an internal organ of a patient.

As indicated in phantom lines at 28, spherical styrofoam indicator element 26 moves in a distal direction when the pressure at distal tip 18 of needle 12 is negative, or below a predetermined standard or reference pressure such as atmospheric pressure. Such a motion of indicator element 26 would occur, for example, upon an accidental piercing of a lung.

As indicated in phantom lines at 30, spherical styrofoam indicator element 26 moves in a proximal direction when the pressure at distal tip 18 of needle 12 is positive, or greater than a predetermined standard or reference pressure such as atmospheric pressure. Such a motion of indicator element 26 would occur, for example, upon a piercing of a spinal column.

Where the pierced organ is an artery, indicator element 26 reciprocates or oscillates relatively rapidly between two extremes (e.g., 28, 30), in synchronism with the beat of the patient's heart.

As further illustrated in FIG. 1, spherical styrofoam indicator element 26 may be connected to housing 20 via a plurality of elastic tethers 32 and 34 or an elastic diaphragm element (see FIG. 2).

As illustrated in FIG. 2, a movable indicator element 36 in housing or chamber 20 of pressure detector and indicator 14 takes the form of an elastic web, i.e., a diaphragm. The periphery of diaphragm 36 is fastened to housing 20 along an inner surface thereof. Diaphragm 36 exhibits a bending type distortion or motion in fluid 22 responsive to, and accordingly indicative of, intraorganic pressures existing at distal tip 18 of needle 12 particularly upon insertion of the distal tip into an internal organ of a patient.

As indicated in phantom lines at 38, diaphragm indicator element 36 bows in a distal direction when the pressure at distal tip 18 of needle 12 is negative, or below a predetermined standard or reference pressure such as atmospheric pressure. As indicated in phantom lines at 40, diaphragm indicator element 36 bows in a proximal direction when the pressure at distal tip 18 of needle 12 is positive, or greater than a predetermined standard or reference pressure such as atmospheric pressure. Where the pierced organ is an artery, indicator element 36 reciprocates or oscillates relatively rapidly between two extremes (e.g., 38, 40), in synchronism with the beat of the patient's heart.

As depicted in FIG. 3, another pressure indicator in housing 20 includes a plurality of reflective particles or fragments of metallic foil 42 dispersed throughout fluid 22. The embodiment of FIG. 3 is effective for detecting arterial entry, as opposed to venous entry. However, it is less effective than the embodiments of FIGS. 1 and 2 in checking for the piercing of a lung or a spinal column.

In a catheterization method using the assembly of FIG. 1, distal end 18 of needle 12 is inserted into a patient, whereupon pressures at the distal tip of the needle are automatically sensed and a qualitative indication of the sensed pressure is provided by the motion of spherical indicator element 26 (or diaphragm 36 or foil particles 42) at a proximal end of needle 12.

When the sensed pressure is arterial, the indicator element 26, 36 or 42 is reciprocated in response to pulsating arterial pressure. Upon the reciprocation of indicator element 26, 36, or 42 in fluid medium 42, needle 12 is removed from the patient and pressure is placed on the patient at an insertion point of needle 12, thereby reducing flow of blood from a punctured artery.

When the sensed pressure is negative owing to entry into a lung, indicator element 26, 36, or 42 moves in a distal direction. Upon an indication of a negative pressure, particularly upon insertion of hypodermic needle 12 in the chest region, the needle is withdrawn from the hole it formed and steps are taken immediately to prevent the flow of air through the hole into the patient's chest.

When the sensed pressure is positive, such as upon insertion of the needle into a vein or the spine, indicator element 26, 36, or 42 moves in a proximal direction. Upon detecting such a motion of the indicator element, a user injects an anaesthetic through needle 12 or through catheter 10 upon insertion of the catheter over the needle and subsequent removal of the needle from the spine.

During an intravenous catheterization procedure, when pressure indicator element 26, 36, or 42 moves in a proximal direction so as to signal an internal pressure in a venous range, i.e., between 10 and 20 mm Hg, catheter 10 is slid over needle 12 into the detected vein, needle 12 is removed and catheter 10 is connected to an intravenous fluid source (not shown).

As illustrated in FIG. 4, in a general embodiment of a catheterization assembly, a hollow hypodermic needle 44 longitudinally traverses a catheter 46 and is connected at a proximal end 48 to a pressure detector or sensor 50 and a pressure indicator 52. Sensor 50 detects pressures inside a patient upon insertion of a distal tip 54 of needle 44 into the patient and indicator 52 qualitatively indicates the sensed pressure.

As depicted in FIG. 5, sensor 50 includes a first array of strain gauges 56 attached, for example, to one side of a diaphragm (e.g., 36 in FIG. 2) and a second array of strain gauges 58 attached to the other side of the diaphragm (not shown). Strain gauges 56 and 58 are operatively connected to a bank of current detectors 60 in turn connected to a group of comparators 62. In response to the electrical currents measured by detectors 60 and the outputs of comparators 62, a signal generator 63 produces one or more signals encoding the direction and possibly the extent of deformation of the gauge-carring diaphragm. These signals may be shown directly on an LCD display 64 constituting indicator 52. Generally, it is contemplated that the display of the measured pressures does not include a scale or other quantification information.

The signals from generator 63 may be processed by logic circuitry 66 which determines the nature of the sensed pressure and generates a signal for controlling the formation of a message on display 64. Such a message may be simply "artery," "vein," "lung," etc.

As illustrated in FIG. 6, a movable indicator element 68 disposed in a generally opaque housing or chamber 70 of pressure detector and indicator 14 takes the form of an elastic web, i.e., a diaphragm. The periphery of diaphragm 68 is fastened to housing 70 along an inner surface thereof. Diaphragm 68 exhibits a bending type distortion or motion in fluid 22 responsive to, and accordingly indicative of, intraorganic pressures existing at distal tip 18 of needle 12 particularly upon insertion of the distal tip into an internal organ of a patient. Diaphragm 68 acts like a spring and exhibits a degree of bending distortion or displacement which is proportionate to the forces exerted on the diaphragm due to pressures internal to organs of a patient.

On a distal side of diaphragm 68, chamber 70 is filled with a biocompatible liquid substance 72 such as saline solution or hydrogel. On a proximal side of diaphragm 68, chamber 70 is open to the atmosphere via a slot 74. Slot 74 is traversed by an indicator finger 76 which points to markings of a scale 78. Scale 78 need not be calibrated to provide accurate pressure readings. Instead, the scale may merely provide a qualitative indication of pressure magnitudes and fluctuations. Finger or pointer 76 is connected via a rigid arm 80 to diaphragm 68.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for instance, that a spring element may take a form other than diaphragm 68. A helical spring (not shown) may be disposed in the housing chamber on a proximal side thereof and connected on a distal side to a piston which is reciprocatable in response to intraorganic pressure fluctuations at distal tip 18 of needle 12. Optionally or alternatively, a color indicator may be provided.

A catheterization device and associated method in accordance with the present invention may be also used to detect when an abscess has been reached by the distal tip of the hypodermic needle. An abscess generally has a positive pressure. Upon detecting the attainment of the positive pressure, a user can aspirate fluid, e.g., via the needle or the catheter.

Accordingly, it is to be understood that the drawings and descriptions herein are proffered by way of example to facilitate comprehension of the invention and should not be construed to limit the scope thereof.

What is claimed is:

1. A catheterization device comprising:

a catheter;

a hollow hypodermic needle longitudinally traversing said catheter; and pressure detection means attached to said needle at a proximal end thereof for sensing pressures inside a patient upon insertion of a distal tip of said needle into the patient and for qualitatively indicating the sensed pressure, said pressure detection means including:
   an at least partially transparent housing;
   a fluid in said housing operatively communicating with a lumen of said needle; and
   a movable float element disposed in said fluid in said housing.

2. The device defined in claim 1 wherein said float is in the form of a sphere.

3. The device defined in claim 2 wherein said sphere is made of styrofoam.

4. The device defined in claim 1 wherein said float is elastically connected to said housing.

5. The device defined in claim 1 wherein said float is connected to said housing via a diaphragm.

6. The device defined in claim 1 wherein said movable float element is one of a plurality of movable indicator elements floating in said fluid.

7. A catheterization method comprising the steps of:

providing a catheter and a hollow hypodermic needle longitudinally traversing said catheter;

inserting a distal end of said needle into a patient;

upon insertion of a distal tip of said needle into the patient, automatically sensing pressures at said distal tip;

automatically generating, at a proximal end of said needle, a qualitative indication of the sensed pressure;

upon determining, in response to the qualitiative indication of sensed pressure, that said distal end of said needle has entered an internal organ of a preselected kind, moving said catheter in a distal direction to insert a distal end portion of said catheter into said internal organ; and withdrawing said needle from the patient upon determining that said distal end of said needle has entered said internal organ.

8. The method defined in claim 7 wherein said step of generating includes the step of moving an indicator element disposed in a fluid filled chamber at said proximal end of said needle.

9. The method defined in claim 8 wherein said indicator element floats in said fluid.

10. The method defined in claim 9 wherein said indicator element is in the form of a sphere.

11. The method defined in claim 8 wherein said step of generating includes the step of reciprocating said indicator element in response to pulsating arterial pressure.

12. The method defined in claim 11, further comprising the steps of (i) removing said needle from the patient upon reciprocation of said indicator element and (ii) placing pressure on the patient at an insertion point of said needle, thereby reducing flow of blood from a punctured artery.

13. The method defined in claim 8 wherein the sensed pressure is negative owing to entry into a lung, said step of generating including the step of moving said indicator element in a distal direction.

14. The method defined in claim 13, further comprising the steps of removing said needle from the patient upon the movement of said indicator element in a distal direction and (ii) reinserting said needle into the patient at a different insertion point.

15. The method defined in claim 7 wherein said step of generating includes the step of moving a diaphragm disposed in a housing at a proximal end of said needle.

16. The method defined in claim 7 wherein said internal organ is a vein and the indication of sensed pressure signals an internal pressure in a venous range, further comprising the step of connecting said catheter to an intravenous fluid source upon moving said catheter in a distal direction to insert said distal end portion of said catheter into said internal organ.

* * * * *